(12) United States Patent
Reed (10) Patent No.: US 10,441,385 B2
(45) Date of Patent: Oct. 15, 2019

(54) DENTAL IMPLANT WITH INTERLOCKING AND CENTERING THREADS

(71) Applicant: RTG Scientific, LLC, Austin, TX (US)

(72) Inventor: Gary Reed, Turlock, CA (US)

(73) Assignee: RTG Scientific, LLC, Austin, TX (US)

( * ) Notice: Subject to any disclaimer, the term of this patent is extended or adjusted under 35 U.S.C. 154(b) by 70 days.

(21) Appl. No.: 15/354,429

(22) Filed: Nov. 17, 2016

(65) Prior Publication Data

US 2017/0135788 A1 May 18, 2017

Related U.S. Application Data

(63) Continuation of application No. 14/510,371, filed on Oct. 9, 2014, now Pat. No. 9,687,319, which is a continuation of application No. 13/694,440, filed on Dec. 3, 2012, now Pat. No. 8,875,399, which is a continuation of application No. 12/489,274, filed on Jun. 22, 2009, now Pat. No. 8,337,205.

(51) Int. Cl.
*A61C 8/00* (2006.01)

(52) U.S. Cl.
CPC ............ *A61C 8/0022* (2013.01); *A61C 8/005* (2013.01); *A61C 8/0018* (2013.01); *A61C 8/0068* (2013.01); *A61C 8/0074* (2013.01); *A61C 8/0075* (2013.01); *A61C 8/0086* (2013.01); *Y10T 29/49567* (2015.01)

(58) Field of Classification Search
CPC ... A61C 8/0022; A61C 8/0086; A61C 8/0075; A61C 8/0068; A61C 8/0074; A61C 8/0018; A61C 8/005; Y10T 29/49567; F16B 33/02

See application file for complete search history.

(56) References Cited

U.S. PATENT DOCUMENTS

| 2,788,046 | A | * | 4/1957 | Rosan | ..................... F16B 33/02 285/92 |
|---|---|---|---|---|---|
| 4,810,149 | A | * | 3/1989 | Lee | ......................... F16B 33/02 411/366.3 |
| 5,571,017 | A | | 11/1996 | Niznick | |
| 6,604,901 | B1 | | 8/2003 | Grossberndt et al. | |
| 6,800,079 | B2 | | 10/2004 | Reed | |
| 7,198,488 | B2 | | 4/2007 | Lang et al. | |

(Continued)

*Primary Examiner* — Sarang Afzali
(74) *Attorney, Agent, or Firm* — Womble Bond Dickinson (US) LLP (57) ABSTRACT

A fastener for embedment in bone includes a chevron-shaped thread pattern having a first radial superior surface at an angle beta on a blank relative to a longitudinally extending axis of the fastener, a second radial superior surface at an angle alpha inboard to the first radial superior surface and relative to the longitudinally extending axis such that the two superior surfaces form a V-shape geometry. The fastener further includes a flank surface underlying the second radial superior surface at an angle gamma, the angle gamma defining an angle with the longitudinally extending axis that is 90°, a relief surface underlying the first radial superior surface such that the flank surface and the relief surface form a V-shape geometry, and a radially-outermost surface adjacent to the relief surface and defining a major diameter of the thread pattern, the radially-outermost surface being parallel to the longitudinally extending axis of the fastener.

1 Claim, 11 Drawing Sheets

(56) References Cited

U.S. PATENT DOCUMENTS

| | | |
|---|---|---|
| 2009/0226857 A1 | 9/2009 | Grant |
| 2009/0233256 A1 | 9/2009 | Schroering |
| 2010/0261141 A1 | 10/2010 | Ajlouni et al. |
| 2012/0308961 A1 | 12/2012 | Hurson |

* cited by examiner

DENTAL IMPLANT WITH INTERLOCKING AND CENTERING THREADS

CROSS-REFERENCE TO RELATED APPLICATION

This application is a Continuation of U.S. patent application Ser. No. 14/510,371, filed Oct. 9, 2014, and which is a Continuation of U.S. patent application Ser. No. 13/694,440, filed Dec. 3, 2012, which issued on Oct. 14, 2014 as U.S. Pat. No. 8,875,399, and which is a Continuation of U.S. patent application Ser. No. 12/489,274, filed Jun. 22, 2009, which issued on Dec. 25, 2012 as U.S. Pat. No. 8,337,205, each of which is hereby incorporated by reference in its entirety in this application.

BACKGROUND OF THE INVENTION

Field of the Invention

The invention relates generally to dental implant and more particularly to a dental implant anchoring device with threading which does not compress or exert expanding pressure to the surrounding bone.

Description of the Prior Art

Dental implants have been used as artificial tooth roots on which prosthetic teeth are mounted. A conventional dental implant 1 shown in FIG. 1 has been described in U.S. Pat. No. 7,198,488. The dental implant 1 has a cylindrical anchoring head 2 formed unitarily with a screw element 3. The screw element 3, usually made of titanium with a roughened surface, is to be screwed into the recipient jaw bone. The anchoring head 2 is adapted to have a prosthetic tooth mounted on it.

Figure 1:
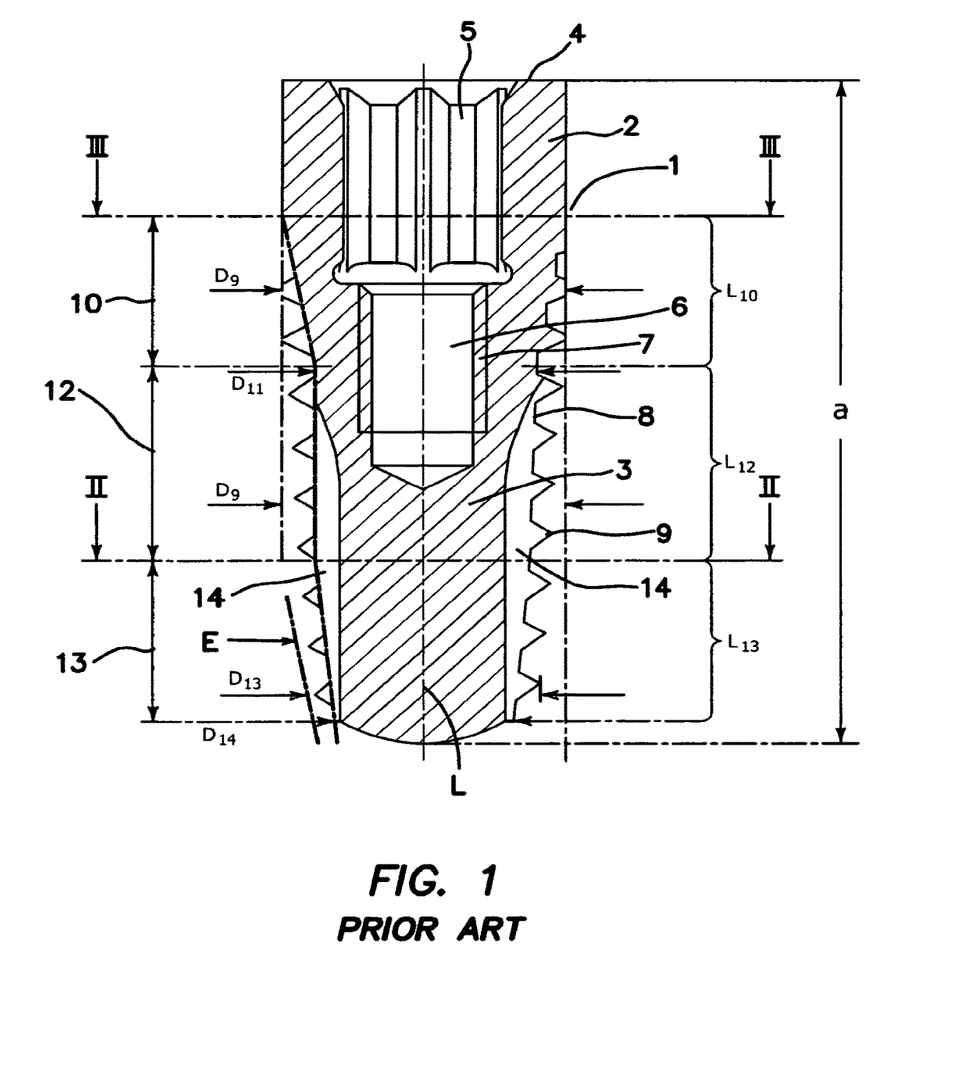
FIG. 1 is a side cross-sectional view which shows a conventional dental implant.

The screw element 3 has a thread core 8 and a self-cutting external thread 9. After being anchored into the bone, it may take months for new bone to grow into close proximity with the surface of the screw element 3. Because of a unique property of roughened titanium, newly grown bone can adhere tightly to the surface of the screw element 3.

BRIEF SUMMARY OF THE INVENTION

An illustrated embodiment of the invention is a dental implant device for insertion into bone, comprising an implant anchor having an interlocking thread helically defined around a longitudinal axis. The thread is adapted to couple to a female threaded bore in the bone.

The dental implant device for insertion into a bore defined in bone for use with a prosthetic tooth or dental appliance, comprising an abutment with a plurality of male keys disposed about the distal end of the abutment, which distal end is capable of being affixed to the prosthetic tooth or dental appliance; an implantable anchor having a proximal and distal end, a plurality of female keyways defined into the proximal end of the anchor, the keyways capable of coupling to the male keys of the abutment and thereby preventing relative rotation of the abutment and anchor; an interlocking thread helically defined around a longitudinal axis of the anchor, the thread being adapted to couple to the bore defined in the bone; and means for coupling the abutment to the implant anchor.

In another embodiment, the dental implant device further comprises a repository bore perpendicular to the longitudinal bore defined in a distal portion of the anchor. The repository bore is cut through the threaded portion of the anchor creating very sharp cutting edges on the face of each thread to allow the threads to become self tapping. The repository bore also serves as a repository for the bone chips created during the thread cutting process. This allows the chips to be moved into and contained within the repository bore preventing galling, interference and radial forces during the thread cutting process. This produces clean cut threads similar to those cut with a tap unlike the incomplete threads cut by the crude and dull edges of prior self tapping devices.

The repository bore of the dental implant comprises a bore defined transversely into the anchor and having an elliptical shape.

The abutment of the dental implant device has a corresponding central longitudinal bore defined through its respective longitudinal ax is, and where the anchor has a central longitudinal bore defined at least partially through its respective longitudinal axis.

The central bore defined through the longitudinal axis of the abutment comprises a clearance bore with an inner smooth surface.

In another embodiment, the central bore defined through the longitudinal axis of the anchor comprises a threaded blind bore with an inner female threaded surface.

In yet another embodiment, the means for coupling the abutment to the anchor comprises a threaded bolt configured to be disposed into the central hollow bores defined through the longitudinal axis of the abutment and the anchor.

The threaded bolt is adapted to threadably engage the inner female threaded surface of the anchor.

In another embodiment, the bolt has a head and where the abutment has a recessed proximal flanged surface and is adapted to receive the head of the threaded bolt in the recessed proximal flanged surface.

In still another embodiment, the means for coupling the abutment to the anchor further comprises means for locking the male keys disposed on the distal end of the abutment into the female keyways disposed on the proximal end of the implant anchor.

In a separate illustrated embodiment a dental implantable device is provided for insertion into bone for use with a prosthetic tooth comprising: an abutment with a plurality of male keys disposed symmetrically about the distal end of the abutment, the prosthetic tooth coupled to the abutment; an implantable anchor with a proximal and distal end and having a plurality of female keyways disposed symmetrically about the proximate end of the implantable anchor capable of coupling to the male keys of the abutment and an interlocking thread helically defined around a longitudinal axis, the thread being adapted to thread into a bore in the bone; means for coupling the abutment to the implantable anchor, and a self-tapping flute defined in a distal portion of the implantable anchor.

In another embodiment, the abutment and implantable anchor each have a corresponding central hollow bore defined along their respective longitudinal axes.

In another embodiment, the means for coupling the abutment to the implantable anchor comprises a threaded bolt arranged and configured to fit through the corresponding central hollow bores defined through the longitudinal axis of the abutment and to thread into the corresponding central hollow bores defined through the longitudinal axis of the implantable anchor.

In yet another embodiment, the means for coupling the abutment to the implantable anchor comprises means for maintaining the male keys disposed on the distal end of the abutment angularly fixed relative to the female keyways disposed on the proximal end of the implantable anchor.

The illustrated embodiment also includes a method of implanting a dental implant into a female threaded portion of bone comprising the steps of self-tapping a male threaded portion of an implantable anchor into a bore defined in bone using a chip repository bore defined in the implantable anchor; tightening the implantable anchor into the bore defined in the bone, wherein tightening the implantable anchor comprises creating a radially interlocking and centering force between the male threaded portion of the implantable anchor and the female threaded portion of the bone; and coupling an abutment to the implantable anchor while preventing relative rotation of the abutment with respect to the implantable anchor.

The method further includes where coupling the abutment to the implantable anchor comprises interlocking a plurality of male keys disposed on the distal end of the abutment to a matching plurality of female keyways defined into the proximal end of the implantable anchor.

In another embodiment, the method step of where coupling the abutment to the implantable anchor comprises inserting a threaded bolt through a defined hollow bore defined along the longitudinal axis of the abutment and the implantable anchor, which bolt maintains at least one key defined on either the abutment or the anchor into a keyway defined into the other one of either the abutment or the anchor.

The embodiment further comprises coupling the threaded bolt with an inner female threaded surface of the implantable anchor and threading the threaded bolt until the bolt head of the threaded bolt contacts an inner recessed flange defined in the abutment.

Finally, in a last embodiment, the method step where coupling the abutment to the implantable anchor further comprises inserting a threaded bolt through a defined hollow bore along the longitudinal axis of the abutment and the implantable anchor; coupling the threaded bolt with an inner female threaded bore of the implantable anchor; and threading the threaded bolt until a bolt head of the threaded bolt contacts an inner recessed flange defined in the abutment.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 2b is a top plan view of the abutment shown in the exploded view of FIG. 2a as seen from section lines 2b-2b in FIG. 2a.

FIG. 2c is a top plan view of the collar shown in the exploded view of FIG. 2a as seen from section lines 2c-2c in FIG. 2a.

FIG. 2d is a top plan view of the anchor shown in the exploded view of FIG. 2a as seen from section lines 2d-2d in FIG. 2a.

FIG. 6 is a side view of the assembled device of FIG. 2a.

FIG. 7a is an exploded side cross-sectional view of a second embodiment which shows a dental implant device having an adjustable unthreaded collar and an internally thread abutment.

FIG. 7b is a top plan view of the shoulder shown in the exploded view of FIG. 7a as seen from section lines 7b-7b in FIG. 7a.

FIG. 7c is a top plan view of the collar shown in the exploded view of FIG. 7a as seen from section lines 7c-7c in FIG. 7a.

FIG. 7d is a top plan view of the anchor shown in the exploded view of FIG. 7a as seen from section lines 7d-7d in FIG. 7a.

FIG. 8 is an assembled side elevational view of the embodiment of FIG. 7a.

FIG. 9b is a top plan view of the shoulder shown in the exploded view of FIG. 9a as seen from section lines 9b-9b in FIG. 9a.

FIG. 9c is a top plan view of the collar shown in the exploded view of FIG. 9a as seen from section lines 9c-9c in FIG. 9a.

FIG. 9d is a top plan view of the anchor shown in the exploded view of FIG. 9a as seen from section lines 9d-9d in FIG. 9a.

FIG. 10 is a side elevational assembled view of the embodiment of FIG. 9a.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Conventional dental implants incorporate screws with standard thread profiles such as acme threads, buttress threads, or circumferential grooves or even holes drilled through the device into which bone may grow to bind the screw. These implants require regeneration of bone to grow into and around the screw, which can take months, to fully anchor. In addition, conventional implants can weaken the implant site as a result of occlusal processes because of the radial spreading forces transferred from the tooth through the screw to the bone by their thread designs and groove geometries.

The illustrated embodiments of the invention provide an interlocking mechanism for an implant anchor. Through a "chevron" shaped external thread geometry on the screw, the implant anchor becomes interlocked with the receiving hole in the bone immediately upon installation. This results in shorter healing time, simplified procedures, reduced cost and less pain for the patient. The chevron thread not only produces better resistance to shear loads during the occlusal processes, but also adds strength to the implant site. These properties lead to better long-term strength and durability for the implant. The stronger fixation provided by the illustrated embodiments of the invention can produce a better platform for the prosthesis in softer portions of the jaw bone such as in molar areas, and may benefit osteoporotic bone as well, which is often too brittle for standard implants.

FIGS. 2a-2d show a dental implant assembly 20 in accordance with an embodiment of the invention. A prosthetic tooth 21 is arranged and configured to be mounted on a top post 22a of an abutment 22. Although the abutment 22 has a generally conical shape to match mating surfaces defined into tooth 21, the right cylindrical post 22b forming the top of abutment 22 may have flat vertical facets 22a as shown in the top view of FIG. 2b of the abutment 22. This allows a torque to be applied to the abutment 22 on the flat surfaces 22a using a wrench or other tool to facilitate screwing abutment 22 into inferior structures in assembly 20 described below.

Figure 2A:
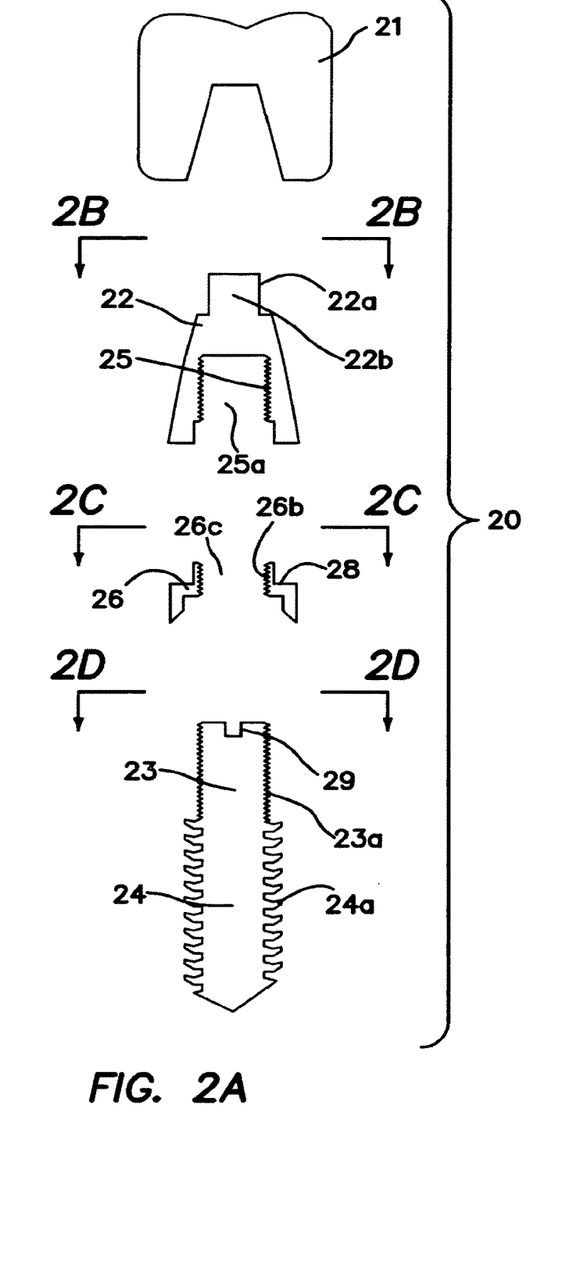
FIG. 2a is an exploded side cross-sectional view which shows components of a dental implant device in accordance with an embodiment of the invention employing a threaded collar and an internally thread abutment.
Figure 2B:
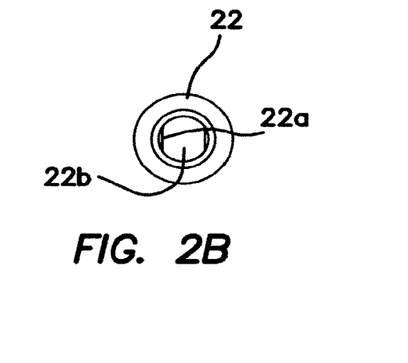
Figure 2C:
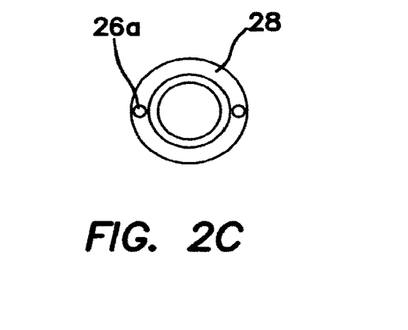
Figure 2D:
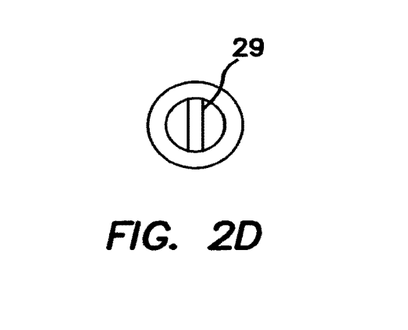
Figure 6:
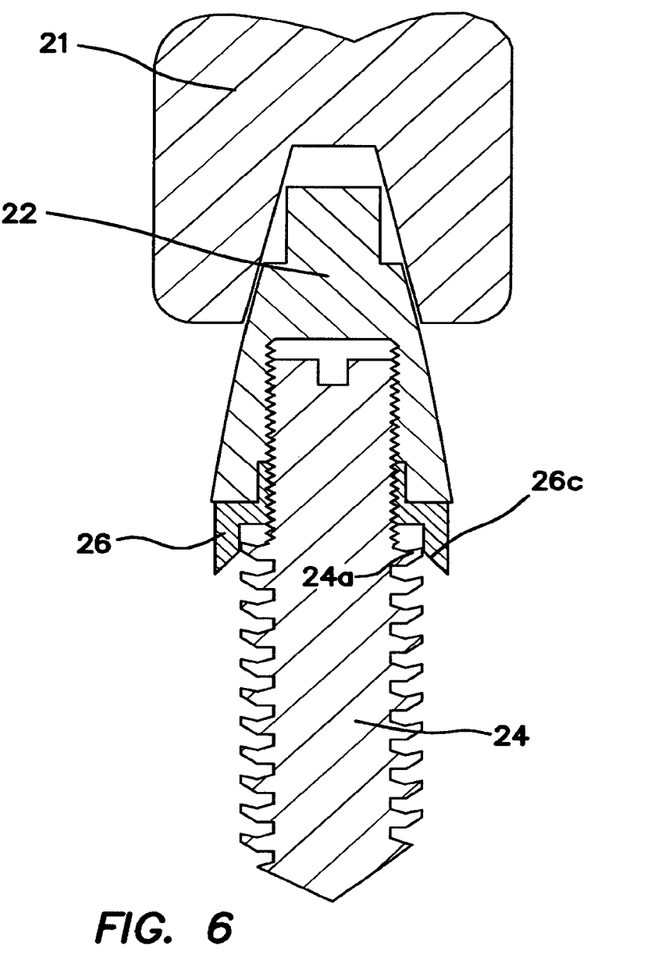
Figures 7A, 7B, 7C, 7D:
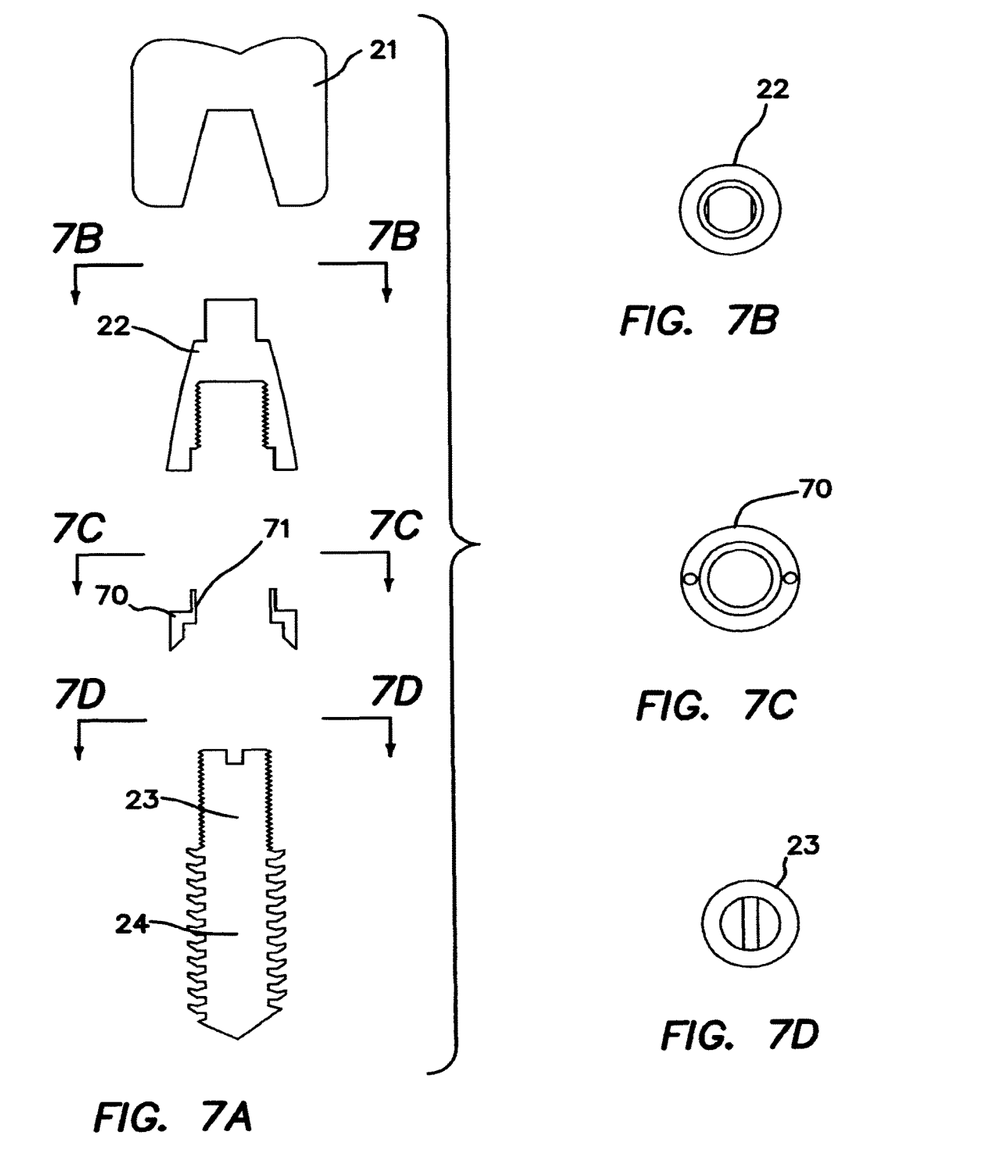

The abutment 22 has an axial bore 25a with an internal thread 25, so that abutment 22 can be threaded onto the external thread 23a of an externally-threaded stem 23 of the implant anchor or screw 24 as best shown in FIG. 6. External threads 23a are arranged and configured to provide mechanical coupling of anchor 24 to collar 28 and abutment 22. Chevron threads 24a are selectively defined in or on the exterior of anchor 24 from or near the lower end of threads 23a to or near the distal end of anchor 24. As shown in FIG. 6, when assembled only chevron threads 24a will be exposed to the bone when implant assembly 20 is completely assembled as intended. Opposing collar 26 is also provided with an axial bore 26c with an internal thread 26b to screw onto thread 23a and engage threaded stem 23. Collar 28 can be selectively adjusted up or down to aid in the implantation procedure as best shown in FIG. 6. The opposing collar 26 also provides a larger-diameter support base on stepped surface 28 for firm support of the lower stepped surface 27 of abutment 22, which is again best depicted in FIG. 6. The bottom surface 27 of the abutment 22 seats against surface 28 of the opposing collar 26. The opposing collar 26 is tightened onto the externally-threaded stem 23 through internal threads 26b, using a spanner wrench applied to holes 26a defined into surface 28 as best shown in FIG. 2c. The implant anchor 24 is tightened into a receiving female hole formed by the oral surgeon in the jaw bone, which hole has threads matching the external threads 24a. Tightening is performed using driving slot 29 defined in the upper end of the implant anchor 24 as depicted to top plan view in FIG. 2d.

Figure 3:
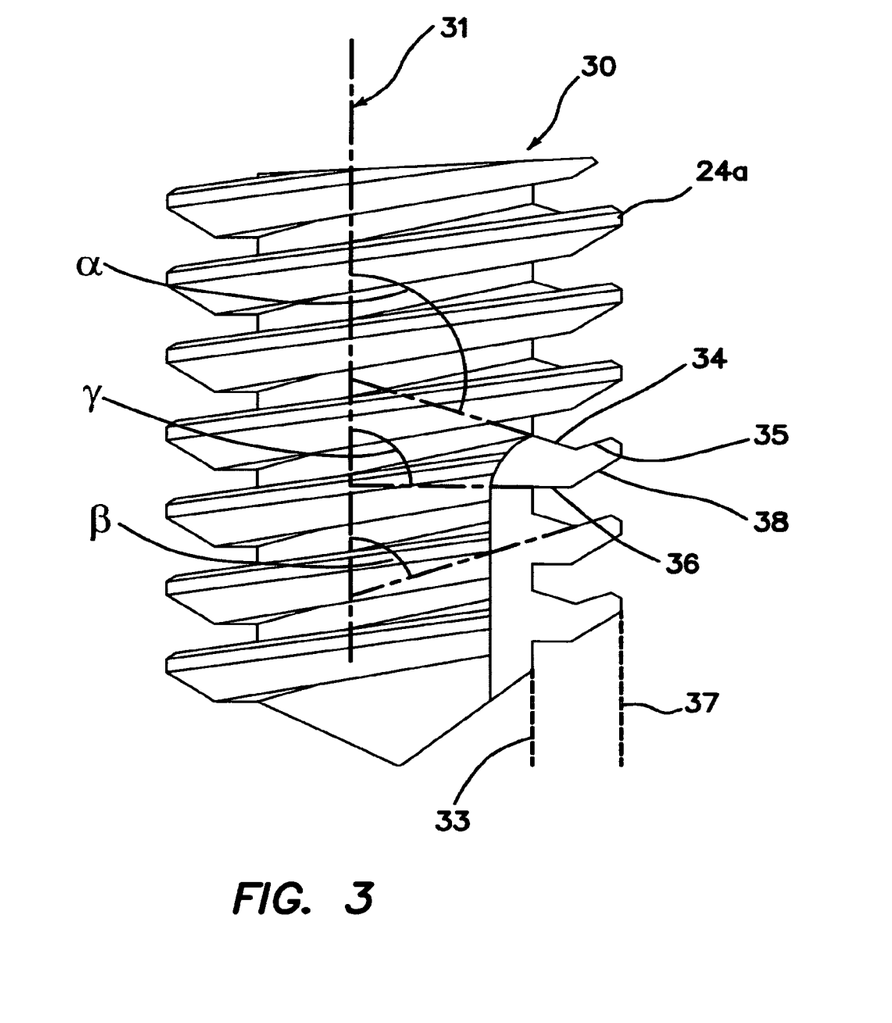
FIG. 3 is a side view of the distal portion of the anchor in enlarged scale which shows a threaded section of the dental implant of the invention, which a lower right partially cut-away side cross-sectional portion.

A distal threaded portion 30 of the implant anchor 24 in accordance with the embodiment of FIGS. 2a-2d is illustrated in enlarged scale in side elevational view in FIG. 3. The threaded section 30 has a generally cylindrical shaped envelope with a longitudinal axis 31. The external thread 24a is defined helically around the circumference of the section 30. The depth of external thread 24a extends between a minor diameter 33 and a major diameter 37 of the threaded section 30.

The external thread 24a has a first superior contact surface 34 and a second more radial superior contact surface 35, an interlocking inferior flank surface 36, and an inferior relief surface 38. When viewed in a side or longitudinal cross-sectional view, the contact surfaces 34 and 35 form an approximate "V" shape, with the flank surface 36 and the relief surface 38 also forming an approximate "V" shape. The thread has an overall "chevron" shape in di cross-sectional view as shown in the partial cut-away side cross-sectional view in the lower right portion of FIG. 3.

Interlocking flank surface 36 forms an angle γ, which in accordance with the embodiment of FIG. 3 is approximately 90 degrees to the axis 31. Contact surface 34 forms an angle α to the axis 31. The angle α is typically greater than the angle γ, e.g., greater than 90 degrees in the embodiment of FIG. 3. The difference between the first and second angles α and γ, together with the upward-angled surface 35, making an acute angle β with respect to axis 31, provide an interlocking interference of the male threaded section 30 to a female threaded receiving hole formed by the oral surgeon in the bone.

Pullout of anchor 24 from the bone is prevented as a result of the angle of contact surface 34 relative to the angle of contact surface 35. A mirror shaped thread formed in the bone mates with surfaces 34 and 35 of anchor 24, so that the mirror surfaces in the bone are juxtapositioned to surfaces 34 and 35 and substantially prevent or limit any radial movement of anchor 24 relative to the bone. Any attempted radial movement of anchor 24 would tend to cause the outer portion of the thread 24a to move downwardly at the angle β due to the overlying bone adjacent to surface 35. However, such movement is blocked or mechanically resisted, because it would tend to drive surface 36 into the opposing juxtapositioned surface of the hone adjacent to surface 36. Hence, anchor 34 is radially locked into place relative to any radial occlusive forces or other forces having a radial component which may be applied to anchor 24. Further, the next lower adjacent thread surface 34 will tend to support the bony material resisting downwardly driven surface 36 in the thread above it, thereby providing a strong backing.

Figure 4:
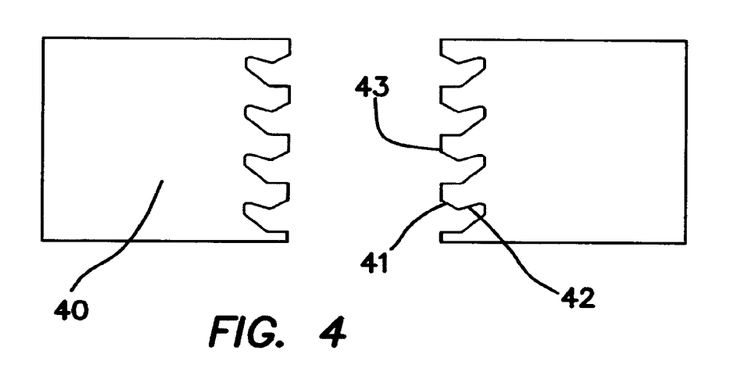
FIG. 4 is a side cross-sectional view of a bone site which shows a female threaded section for receiving the dental implant.

FIG. 4 shows a female threaded portion 40 which is formed in the bone. The female thread teeth 43 are complimentarily shaped to the male thread 24a, and have surfaces 41 and 42 corresponding to surfaces 34 and 35, respectively. The female threaded portion 40 of bone is preferably formed by threading a hole with a tap which is the approximate mirror shape the male threads 24a. In the illustrated embodiment, anchor 24 is not self-tapping and hence no substantial radially compressive forces are normally applied to the bone when a pure torque is applied to anchor 24. However, it must be understood that it is entirely within the spirit and scope of the invention that threads 24a could be modified to assume a self-tapping form if desired.

Figure 5:
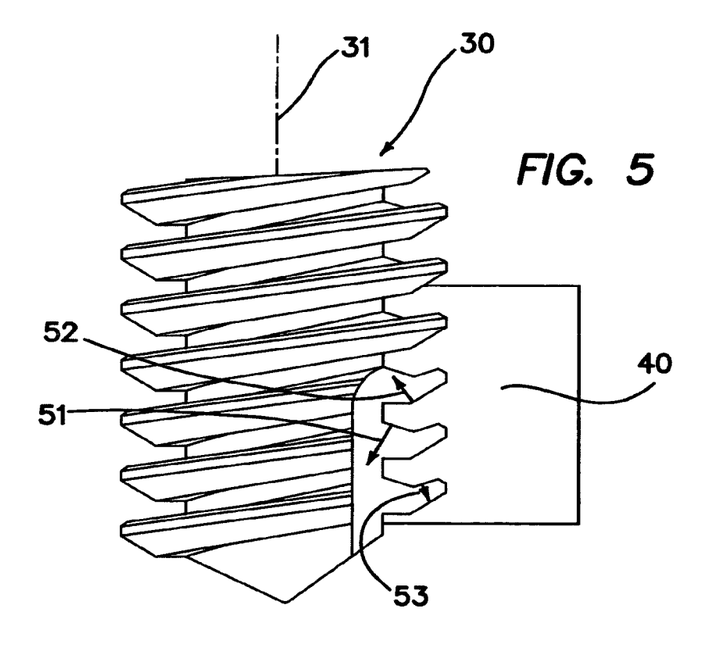
FIG. 5 is a side view of the distal portion of the anchor in enlarged scale which illustrates the reaction forces from the bone applied to the threaded section of the dental implant with a partially cut-away section of the anchor shown in side cross-sectional view coupled to the female threaded section in the bone site as shown in side cross-sectional view.

FIG. 5 is a side elevational view of the male threaded portion 30 of FIG. 3 engaged with a side cross-sectional view of the female threaded portion 40 of bone with a partially cut-away section of die anchor 24 shown in side cross-sectional view. In such an engaged state, an interlocking joint is created as described above. As the connection between the male threaded portion 30 and the female threaded portion 40 is tightened, surfaces 34 and 35 bear against surfaces 41 and 42, respectively. A centering force is generated between the female threaded portion 40 and the male threaded portion 30 because of the chevron shape. This centering force is uniformly and helically distributed around the circumference of the mating threads when engaged. This centering force prevents spreading or drawing of the joint between the anchor 24 and the threaded hole in the bone.

A vector reactive force from the bone illustrated as arrow 51 in FIG. 5 acts upon the contact surface 34 of thread 24a by surface 41 of the tapped bone, and a vector reactive force from the bone illustrated as arrow 52 acts upon the surface 38 of thread 24a by means of surface 42 of the tapped bone. Both vector forces 51 and 52 have an inward radial component toward the axis 31, which radial component is determined by the angle of the reactive surfaces and their areas. Similarly, a reactive vector force from the bone represented by arrow 53 acts upon the contact surface 35 of thread 24a by surface 42 of the tapped bone and has an outward radial component away from the axis 31. The vector sum forces 51, 52 and 53 prevent the threaded portion 30 of anchor 24 from radially sliding with respect to the female threaded portion 40 of the tapped bone, or provide a net centering force.

FIG. 6 shows the assembled device 20 with the opposing collar 26 overlying the threads 24a of the implant anchor 24. When tightened, the downward-angled surface 26c of the opposing collar 26 creates a reaction force from the bone which opposes the reaction force from the bone arising from upward-angled thread 24a, thereby creating a longitudinal clamping force.

Figure 8:
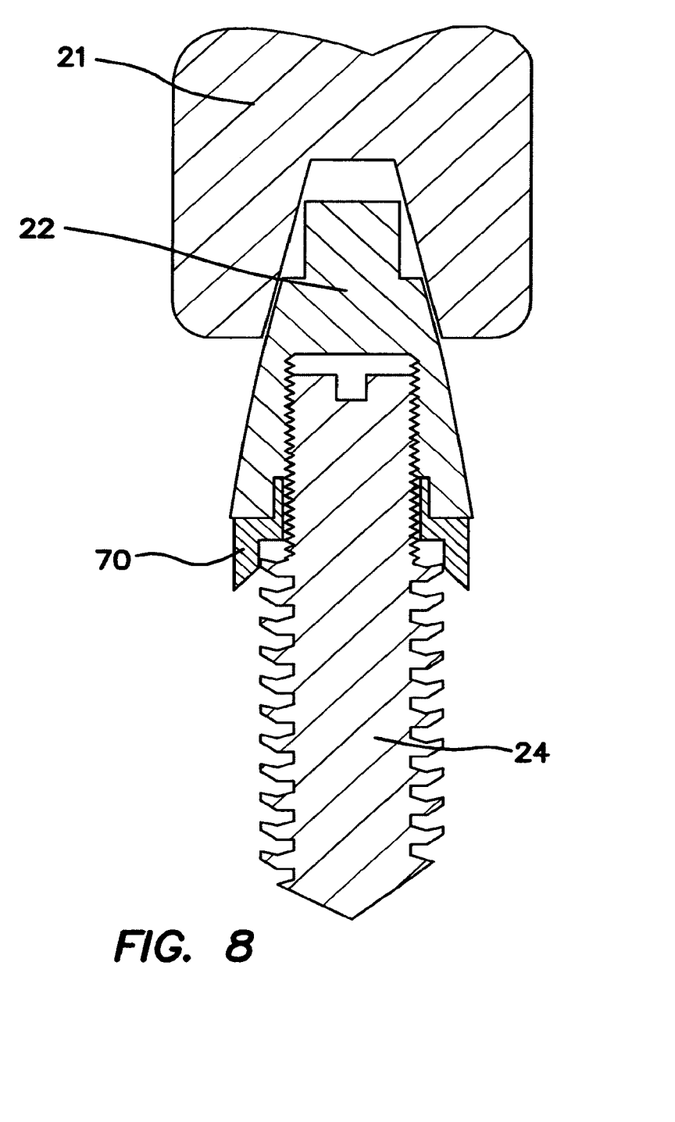
Figure 9A:
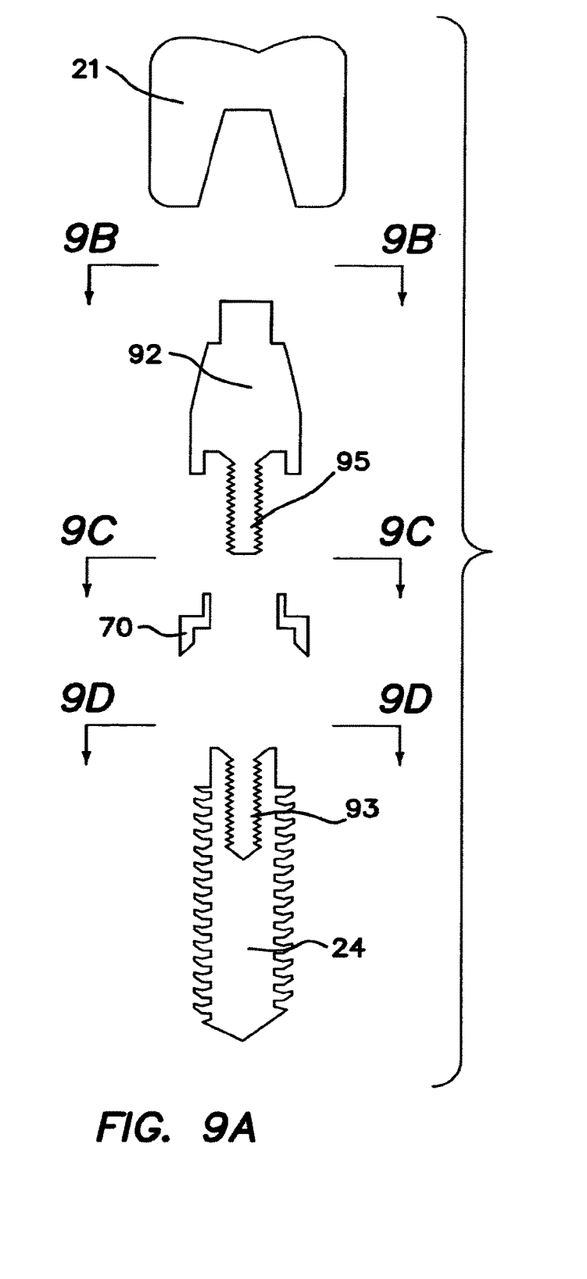
FIG. 9a is an exploded side cross-sectional view of a third embodiment which shows a dental implant device having an adjustable unthreaded collar and an externally threaded shaft extending distally from the abutment.
Figure 9B:
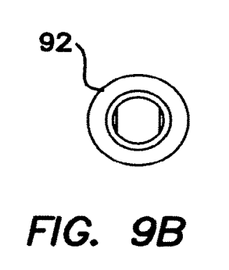
Figure 9C:
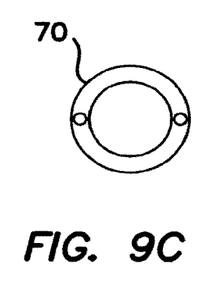
Figure 9D:
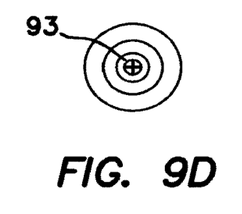

FIGS. 7a-7d show an opposing collar 70 in accordance with another illustrated embodiment of the invention. The embodiment of FIGS. 7a-7d differs from that of FIGS. 2a-2d in that collar 70 has a relatively smooth inner bore 71 without threading. This allows the abutment 22 to force the opposing collar 70 downward as it is threaded onto the threaded portion 23 of the implant anchor 24 creating a clamping force against the bone due to tightening of abutment 22 instead of tightening of collar 70. The assembled view of this device is shown in FIG. 8.

Figure 10:
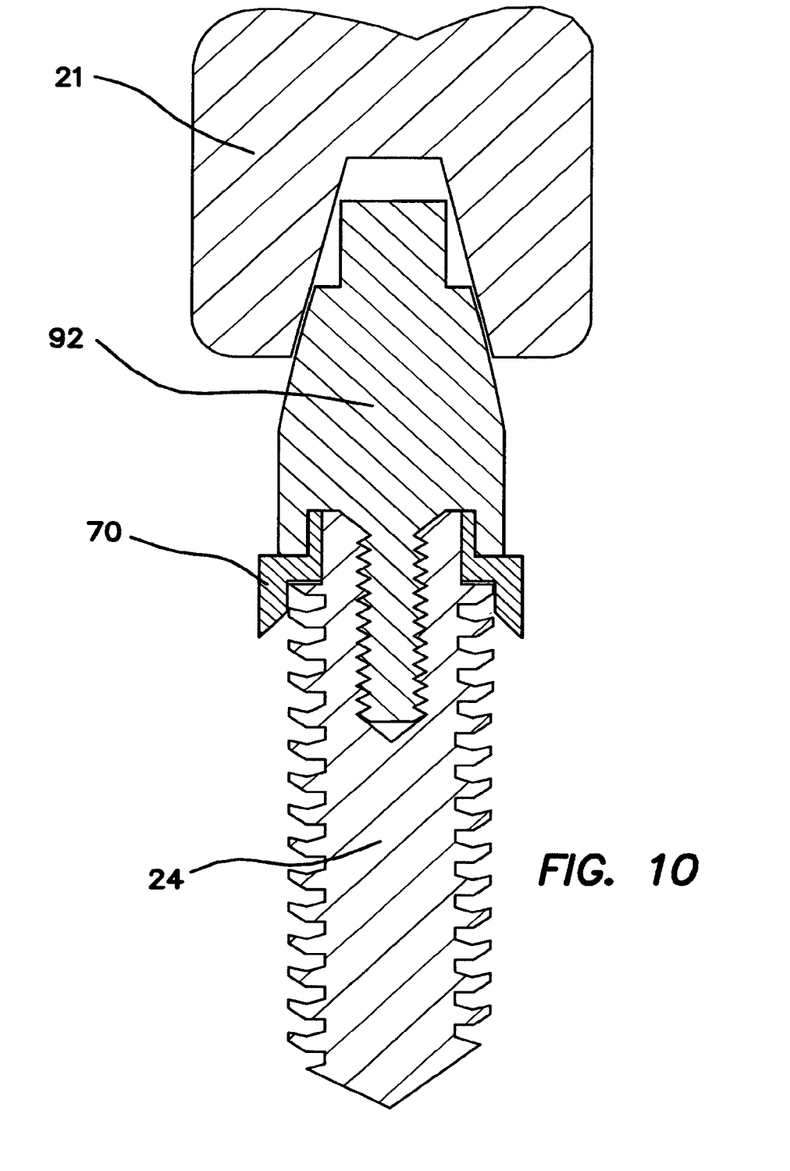

FIGS. 9a-9d are views which show yet another illustrated embodiment where the abutment 92 is provided with a male threaded distal shaft 95 instead of an internal female threaded portion 25 as in the above embodiments. The threaded shaft 95 couples to the implant anchor 24 within an axially defined female threaded hole 93. FIG. 10 is a side cross-sectional view which shows an assembled implant assembly 20 of FIGS. 9a-9d.

FIGS. 11-14 depict an alternative embodiment of the implant anchor and abutment, denoted for this embodiment as references 100 and 108 respectively.

Figure 11:
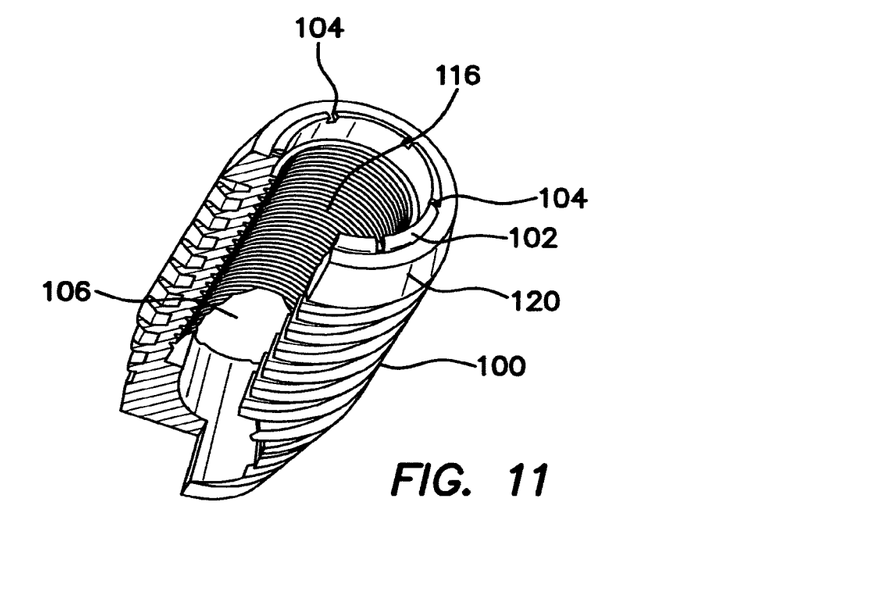
FIG. 11 is a partial cut-away, three-quarter perspective view of the anchor with a cross section removed so as to clearly see the repository bore embodiment.

As best seen in FIG. 11, the implant anchor 100 comprises a collar 120 at its proximal end. The collar 120 further comprises a collar ring 102 disposed on the top of the collar 120. The collar ring 102 comprises a plurality of female keyways 104 that are located symmetrically about the collar ring 102. The keyways 104 depicted are defined as square indentations, but other shapes, placements or numbers of keyways in the collar ring 102 here may also be used by the skilled artisan without departing from the original spirit and scope of the invention. In the preferred embodiment, anchor 100 is an integral or single piece machined element, but may be comprised of joined portions if desired.

Figure 13:
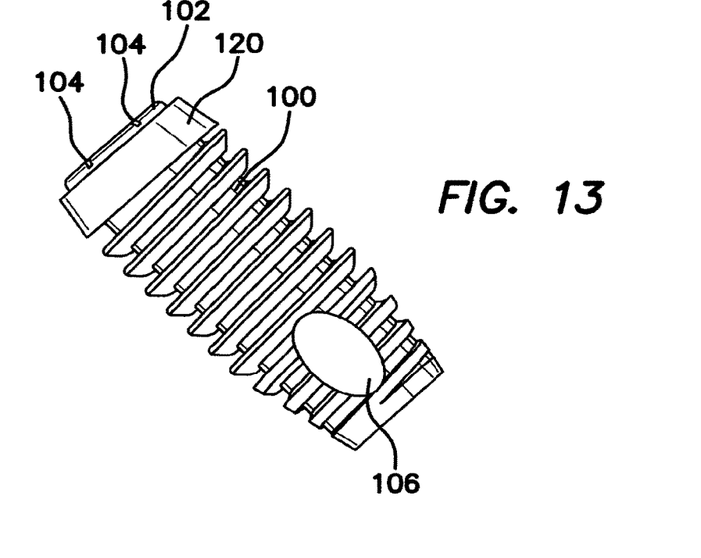
FIG. 13 is a side plan view of the anchor shown in FIG. 11.

Also seen in FIG. 11 is a hollow blind bore defined on the longitudinal axis of the implant anchor 100 with an inner female threaded surface 116 that is disposed throughout the bore. At the distal end of the implant anchor 100 is a large elliptical repository bore 106. The repository bore 106 comprises at least two diametrically opposed openings defined through the wall of the implant anchor 100 near the end of the blind bore that are arranged so that a hole or opening is present through the entire diameter of the implant anchor as best seen in FIG. 13. In the illustrated embodiment, repository bore 106 is partially defined through the bore and partially defined through the solid lower end portion of anchor 100 in approximately equal fractions, although placement with respect to the bore is not critical. However, it can be seen that it is advantageous to have repository bore 106 begin in the wall of anchor 100 at approximately the lowest level of the exterior threading so that chip relief is available into repository bore 106 at or near where bone cutting by the exterior threading will first occur. Repository bore 106 renders the implant anchor 100 self-tapping when being inserted into the bone of a patient, because bone material that has been removed or cut by the external threads of the implant anchor 100, is removed from or clears the threads and enters the implant anchor 100 through the repository bore 106 as the anchor 100 is being turned into the bone. This process then clears the bone debris away from the threads of the implant anchor 100 and stores it within the anchor 100 itself, thus lowering the probability of any bone debris becoming stuck or jammed within the threads of the device and preventing possible galling. The repository bore 106 is defined as elliptical openings in FIGS. 11, 13, and 14, however it is to be expressly understood that fewer or additional openings or other shapes others than those shown may be used by the skilled artisan without departing from the original spirit and scope of the invention.

Figure 12:
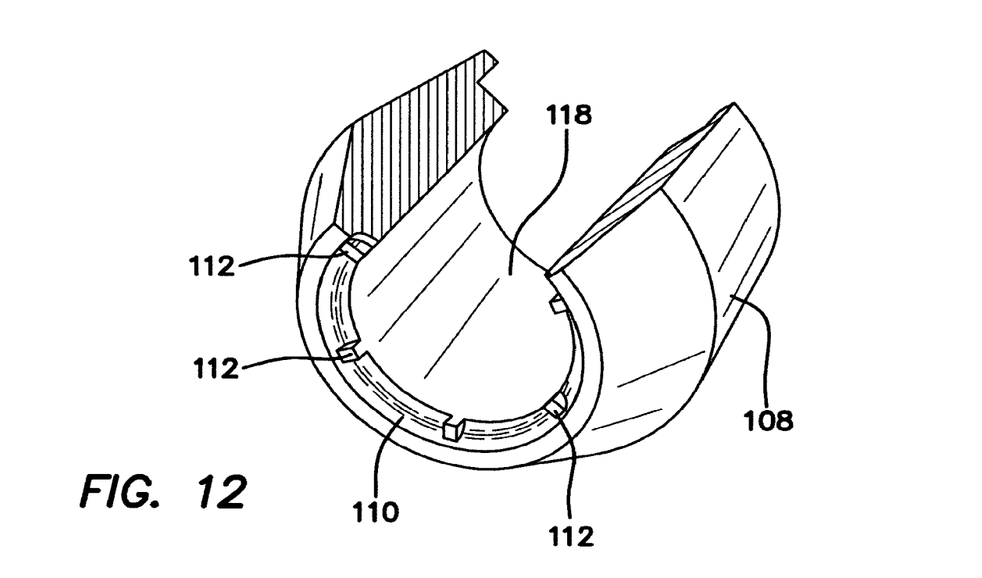
FIG. 12 is a partial cut-away, three-quarter perspective view of the abutment with a cross section removed so as to clearly see the smooth inner surface of the abutment.

In FIG. 12, an alternative embodiment of the abutment 108 is shown. The abutment 108 comprises a recessed inner flange 110 disposed on its distal or lower end. The inner flange 110 further comprises a plurality of male keys 112 located symmetrically around the inner flange 110. The keys 112 depicted are of a square shape to match and easily slip into the keyways 104 defined in collar ring 102, but other shapes or numbers of pegs in the inner flange 110 not shown here may also be used by the skilled artisan without departing from the original spirit and scope of the invention. Additionally, the abutment 108 comprises a hollow bore 118 defined through its longitudinal axis with a smooth inner surface throughout as seen in FIG. 12. Bore 118 provides a clearance hole for a bolt which secures abutment 108 to anchor 100 as described below in connection with FIG. 14.

The abutment 108 couples to the implant anchor 108 via the male keys 112 disposed on the inner flange 110 of the abutment 108 and the female keyways 104 disposed on the collar ring 102 of the implant anchor 100 to create an anti-rotation lock which prevents abutment 108 from rotating with respect to anchor 100 after it is secured thereto. As is known in the art, abutment 108 need not be a straight cylinder as shown in FIG. 12, but may include a variety of inclined or angled shapes. A dental crown or other dental appliance (not shown) will later be attached to abutment 108 and in the event that the receiving bore in the jaw has not been perfectly drilled at the correct angle, the angular misalignment of anchor 100 in the jaw may be compensated by selecting an abutment 108 of approximately equal inclination and then setting the inclined abutment 108 at the correct compensating azimuthal position on anchor 100 to effectively take out the angular misalignment of anchor 100. The number and spacing of keys 112 and keyways 104 are such to allow a plurality of mechanically strong, but finely adjustable relative azimuthal settings between anchor 100 and abutment 108 when the two elements are assembled together and then mechanically secured together by bolt 114. The dental crown or other dental appliance will then be provided with a an angularly oriented abutment 108 for affixation, which is angularly oriented with respect to the surrounding teeth and dental structures as if the receiving bore fir anchor 100 had been perfectly and correctly drilled. Including an adjustable, positive, mechanical, anti-rotation lock between abutment 108 and anchor 100 is advantageous for securing this relative angular orientation between abutment 108 and anchor 100 at all later times notwithstanding forces with may be applied to the crown or dental appliance which may tend to disturb its initial angular set in the jaw.

Figure 14:
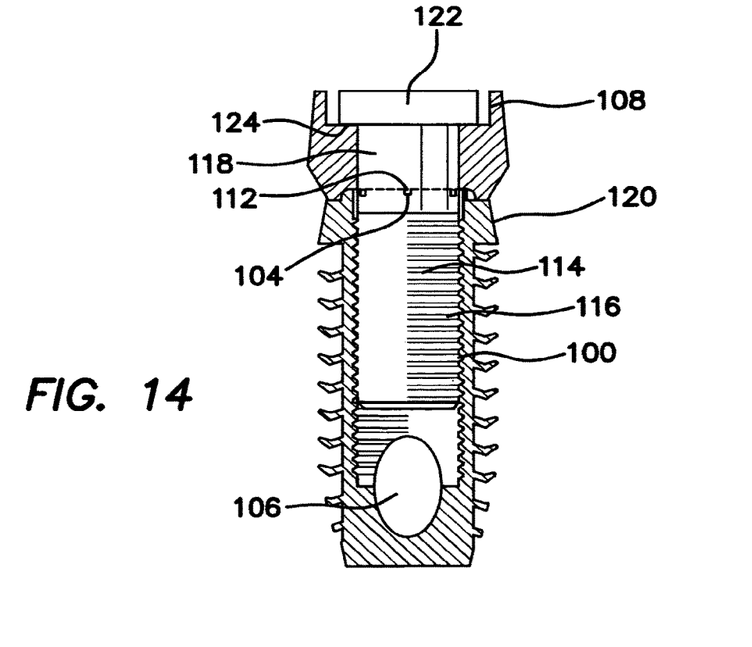
FIG. 14 is a side longitudinal cross sectional view of the assembled anchor and abutment coupled together via a threaded bolt.

First, after the implant anchor 100 has been successfully inserted into the patient's bone, the user lines up the male keys 112 of the abutment 108 with the female keyways 104 of the anchor 100 and then inserts the keys 112 into the keyways 104 until the inner ring 108 is flush against the collar ring 120 as seen in FIG. 14. The keys 112 are arranged on the abutment 108 such that the abutment 108 will not be capable of being pressed flush against the anchor 100 until every key 112 has been correctly inserted into its corresponding keyway 104. Once the abutment 108 is firmly coupled to the proximal end of the anchor 100, a threaded bolt 114 is inserted through the top of the abutment 108. The bolt 114 is pushed through the smooth inner surface 118 of the abutment 108 until meeting the interior threading 116 defined in anchor 100. Once in the anchor 100, the threaded bolt 114 engages the inner female threading 116 of the implant anchor 100 as seen in FIG. 14. The bolt 114 is threaded or tightened down the longitudinal axis of the implant anchor 100 but its lower end is stopped before overlapping the opening of repository bore 106 when the head 122 of the threaded bolt 114 meets the inner recessed surface 124 within the abutment 108. The bolt 114 along with the coupling of the keys 112 and keyways 104 provides an effective means for firmly coupling the abutment 108 to the implant anchor 100 and strengthening to the overall structure of the device by reducing the probability of any shifting or loosening of the abutment 108 from the anchor 100 when an off-axis load is applied to the device, for example when the patient is chewing or speaking. The bolt 114 is sufficiently long enough to extend a predetermined distance into the implant anchor 100, but does not extend so far as to block or interfere with the opening of the repository bore 106 and therefore impede the bone debris clearing process described above.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments. For example, the thread may not have all of the first contact surface, the second contact surface, the flank surface, and the relief surface, so long as one surface, such as the second surface, provides means for preventing the thread from sliding away from the female threaded portion. On the other hand, more surfaces may be provided. In addition, the surfaces may be angled differently from those shown in the exemplary drawings.

Further although in the illustrated embodiment the keys are defined in the abutment and the keyways are defined in the anchor, it is entirely within the scope of the invention that this choice could be reversed. Namely, the keys could be defined in the anchor and the keyways in the abutment. Therefore, the claims below must be construed to include the notion that keys and keyways may be reversed with respect to their position in the recited elements.

Therefore, it must be understood that the illustrated embodiment has been set forth only for the purposes of example and that it should not be taken as limiting the invention as defined by the following claims. For example, notwithstanding the tact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

The invention claimed is:

1. A fastener for embedment in bone, comprising:
   a thread pattern which is chevron-shaped in section and has a first radial superior surface cut at an angle beta relative to a longitudinally extending axis of the fastener and has a second radial superior surface cut at an angle alpha inboard to the first radial superior surface and relative to the longitudinally extending axis such that the two superior surfaces cooperate to form a V-shape geometry:
   a flank surface underlying the second radial superior surface relative to a direction of embedment in the bone, and cut at an angle gamma, the angle gamma defining an angle with the longitudinally extending axis that is 90°;
   a relief surface underlying the first radial superior surface relative to the direction of embedment in the bone, and cut at an acute angle outboard to the flank surface and relative to the longitudinally extending axis, such that the flank surface and the relief surface cooperate to form a V-shape geometry; and
   a radially-outermost surface adjacent to the relief surface and defining a major diameter of the thread pattern, the radially-outermost surface being parallel to the longitudinally extending axis of the fastener.

* * * * *